US012491138B2

(12) United States Patent
Patel et al.

(10) Patent No.: US 12,491,138 B2
(45) Date of Patent: *Dec. 9, 2025

(54) AUTOMATIC MEDICATION INTAKE AND DISPENSING SYSTEM

(71) Applicants: Pratham Raju Patel, Chicopee, MA (US); Buuthien Hang, Stoughton, MA (US)

(72) Inventors: Pratham Raju Patel, Chicopee, MA (US); Buuthien Hang, Stoughton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/197,983

(22) Filed: May 3, 2025

(65) Prior Publication Data

US 2025/0339347 A1 Nov. 6, 2025

Related U.S. Application Data

(63) Continuation of application No. 19/197,981, filed on May 3, 2025.

(Continued)

(51) Int. Cl.

*A61J 7/00* (2006.01)
*A61B 5/0205* (2006.01)
*G16H 20/13* (2018.01)

(52) U.S. Cl.

CPC ........... *A61J 7/0084* (2013.01); *A61B 5/0205* (2013.01); *A61J 7/0069* (2013.01); *G16H 20/13* (2018.01); *A61J 2200/70* (2013.01)

(58) Field of Classification Search

CPC .... G07F 17/0092; G16H 20/13; A61J 7/0084; A61J 7/0481; A61J 2200/30; A61J 7/0454

See application file for complete search history.

(56) References Cited

U.S. PATENT DOCUMENTS 6,036,812 A 3/2000 Williams et al.
8,060,248 B1 11/2011 Boyer et al.

(Continued)

FOREIGN PATENT DOCUMENTS

WO 2006102409 9/2006
WO 2014199374 12/2014

(Continued)

*Primary Examiner* — Timothy R Waggoner

(74) *Attorney, Agent, or Firm* — Law Office of Ilya Libenzon

(57) ABSTRACT

An automatic medication intake and dispensing system is disclosed. The system enhances medication adherence and facilitates health monitoring by employing NFC-tagged medication bottles that communicate prescription data to an integrated NFC reader. A mechanical arm transfers medication into a rotational storage tray with designated compartments. At scheduled times, the system automatically retrieves the appropriate medication using a vacuum-assisted mechanism and delivers it to the user. If a dose is missed, the system initiates retry and alert protocols. Integrated telehealth capabilities include video and audio transmission, along with vital sign monitoring modules for measuring blood pressure, heart rate, and blood oxygen levels. A temperature sensor is also incorporated. A single-board computer manages system operations and uploads data, including missed doses and health metrics, to a secure cloud platform for access by patients, caregivers, and healthcare providers. The system provides secure prescription management, automated dispensing, and continuous health data collection.

14 Claims, 10 Drawing Sheets

Related U.S. Application Data

(60) Provisional application No. 63/769,749, filed on Mar. 11, 2025, provisional application No. 63/642,752, filed on May 4, 2024.

(56) References Cited

U.S. PATENT DOCUMENTS

| | | | | |
|---|---|---|---|---|
| 8,862,266 | B2 | 10/2014 | Van Ooyen et al. | |
| 9,498,408 | B2 * | 11/2016 | Lehmann | G16H 10/60 |
| 11,554,081 | B1 * | 1/2023 | Gellman | G16H 10/65 |
| 11,583,477 | B2 | 2/2023 | Herman et al. | |
| 2002/0113077 | A1 | 8/2002 | Topliffe et al. | |
| 2002/0147526 | A1 | 10/2002 | Siegel | |
| 2017/0020785 | A1 | 1/2017 | Mccullough | |
| 2017/0132867 | A1 * | 5/2017 | Berg | A61J 7/0481 |
| 2019/0130078 | A1 | 5/2019 | Herbert et al. | |
| 2019/0228851 | A1 * | 7/2019 | Rawal | G16H 20/13 |
| 2021/0283019 | A1 | 9/2021 | Nelson | |
| 2023/0140779 | A1 | 5/2023 | Bouthiette | |

FOREIGN PATENT DOCUMENTS

| | | |
|---|---|---|
| WO | 2016141102 | 9/2016 |
| WO | 2023178351 | 9/2023 |

* cited by examiner

AUTOMATIC MEDICATION INTAKE AND DISPENSING SYSTEM

TECHNICAL FIELD

The present disclosure relates to the field of healthcare technology, specifically to systems and devices for automated medication dispensing and health monitoring.

BACKGROUND

Medication management and health monitoring are critical components of healthcare, particularly for individuals with chronic conditions, elderly patients, or those managing complex medication regimens. Conventional methods, such as manual pill organizers or basic electronic timers, frequently result in missed doses, non-adherence, and a lack of real-time data availability for patients and caregivers. Although existing automated medication dispensers address some of these challenges, they often lack advanced prescription management capabilities, secure intake verification, integrated health monitoring modules, and robust real-time feedback and notification systems. The absence of a cohesive framework linking medication adherence with biometric monitoring creates care gaps that may hinder timely intervention. Accordingly, there remains a need for a comprehensive system that securely manages prescriptions, automates dispensing with reliable feedback mechanisms, and continuously monitors health parameters.

The present disclosure addresses these needs by providing a system that integrates secure near-field communication (NFC) technology, an automated rotational dispensing mechanism, a vacuum-assisted outtake and mechanical intake apparatus, and a plurality of health-monitoring modules, all coordinated under the control of a single-board computer.

SUMMARY OF THE EMBODIMENTS

The present disclosure relates to an automatic medication intake and dispensing system configured to enhance medication adherence while collecting critical health data. The system employs near-field communication (NFC)-tagged medication bottles which, when placed into the device, communicate prescription data to an NFC reader. A mechanical arm with integrated feedback sensors transfers the medication into a rotational storage tray composed of wedge-shaped compartments, each allocated for a particular medication type.

At the time of a scheduled dose, the rotational tray advances to align the appropriate compartment with a dispensing mechanism. A vacuum-based retrieval system, operating in coordination with a motorized linear movement assembly, extracts the designated medication from the selected compartment and delivers it to the user, for example, by depositing the medication into a dispensing cup. If the user fails to retrieve a dispensed medication or misses a scheduled dose, the system initiates retry mechanisms and issues alerts to promote adherence.

The system further incorporates on-board video and audio transmission capabilities, utilizing an integrated camera and microphone, to facilitate telehealth interactions. In addition, the system supports interchangeable vital sign monitoring modules configured to measure parameters such as blood pressure, heart rate, and blood oxygen levels, and includes a temperature sensor positioned on the front surface. All operational control and data management functions are handled by a single-board computer, which securely uploads relevant information, including missed doses and abnormal vital sign readings to a cloud platform accessible by patients, caregivers, and healthcare providers. Through this integrated approach, the present disclosure provides secure prescription management, precise automated dispensing, and continuous health monitoring.

Other aspects, embodiments and features of the system and method will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the device and method shown where illustration is not necessary to allow those of ordinary skill in the art to understand the device and method.

BRIEF DESCRIPTION OF THE DRAWINGS

The preceding summary, as well as the following detailed description of the disclosed system and method, will be better understood when read in conjunction with the attached drawings. It should be understood, however, that neither the device nor the method is limited to the precise arrangements and instrumentalities shown.

DETAILED DESCRIPTION OF SPECIFIC EMBODIMENTS

Figure 1:
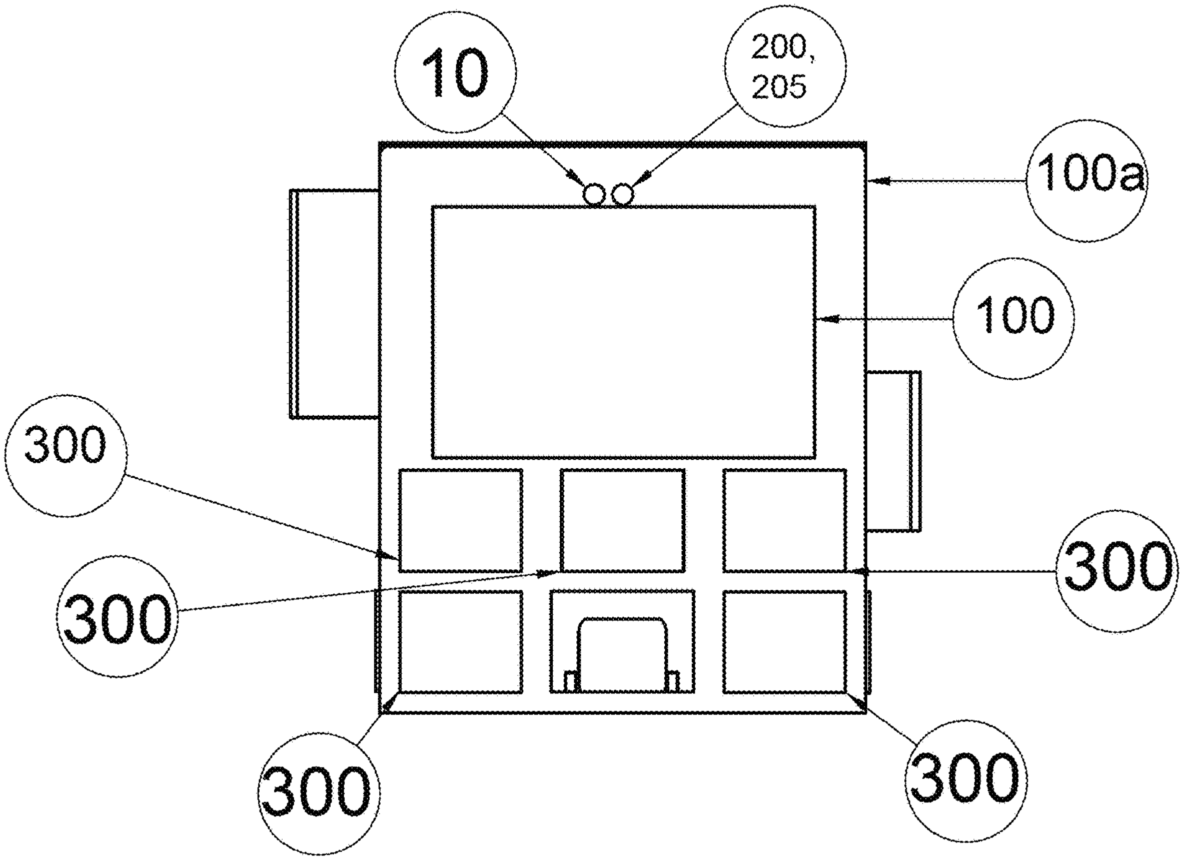
FIG. 1 is a front view of the automatic medication intake and dispensing system, in accordance with embodiments of the present disclosure.

The following detailed description is provided to enable a person of ordinary skill in the art to make and use the embodiments of the present disclosure. Various modifications, substitutions, and variations will be apparent to those of ordinary skill in the art without departing from the scope of the disclosure. Reference is made to the accompanying drawings, which are provided for purposes of illustration and are not intended to limit the scope of the disclosure. It should be understood that the features illustrated and described with respect to one embodiment may be combined with features of other embodiments without departing from the spirit and scope of the present disclosure.

Throughout the drawings and the following description, like reference numerals may refer to similar or identical elements for clarity and consistency. The embodiments described herein relate to an automatic medication intake and dispensing system configured to enhance medication adherence and facilitate continuous health monitoring, as described in greater detail below.

Referring now to the drawings, an automatic medication intake and dispensing system is described in accordance with embodiments of the present disclosure. As shown in FIGS. 1 through 8, the system is enclosed within a housing 100*a* featuring a touchscreen panel 100 for user interaction. Through the touchscreen interface, patients may configure settings, view medication schedules, receive adherence notifications, and monitor vital signs in real time.

Figure 2:
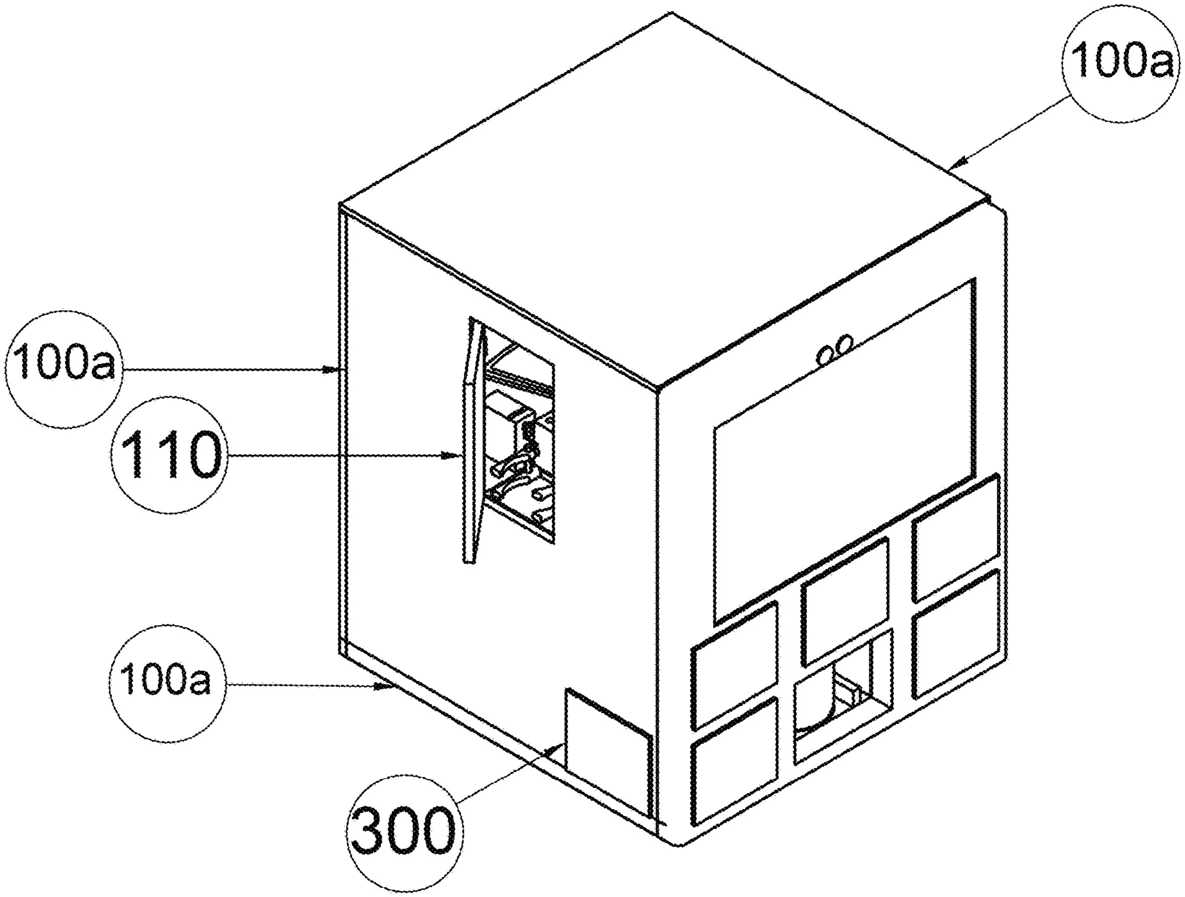
FIG. 2 is a northwest isometric perspective view of the system, in accordance with embodiments of the present disclosure.
Figure 3:
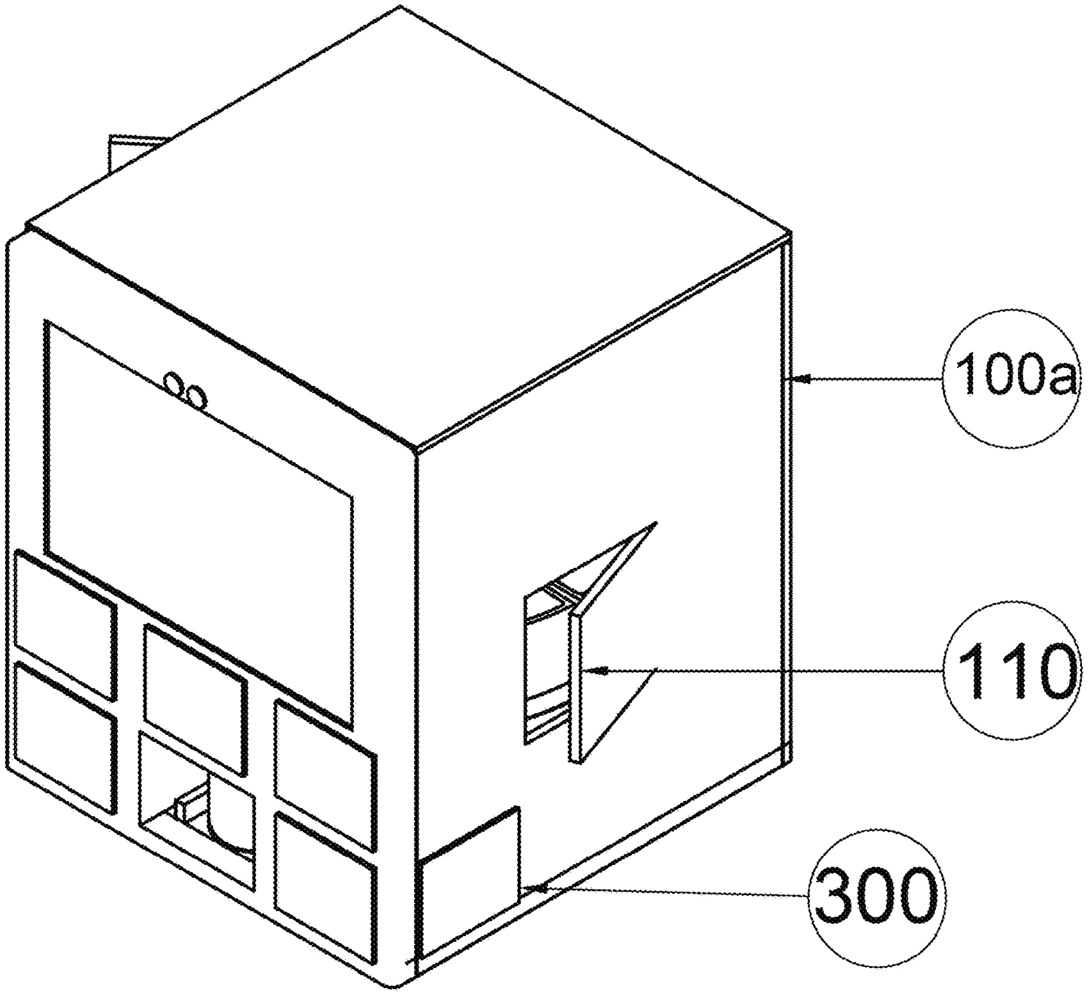
FIG. 3 is a northeast isometric perspective view of the system, in accordance with embodiments of the present disclosure.
Figure 4:
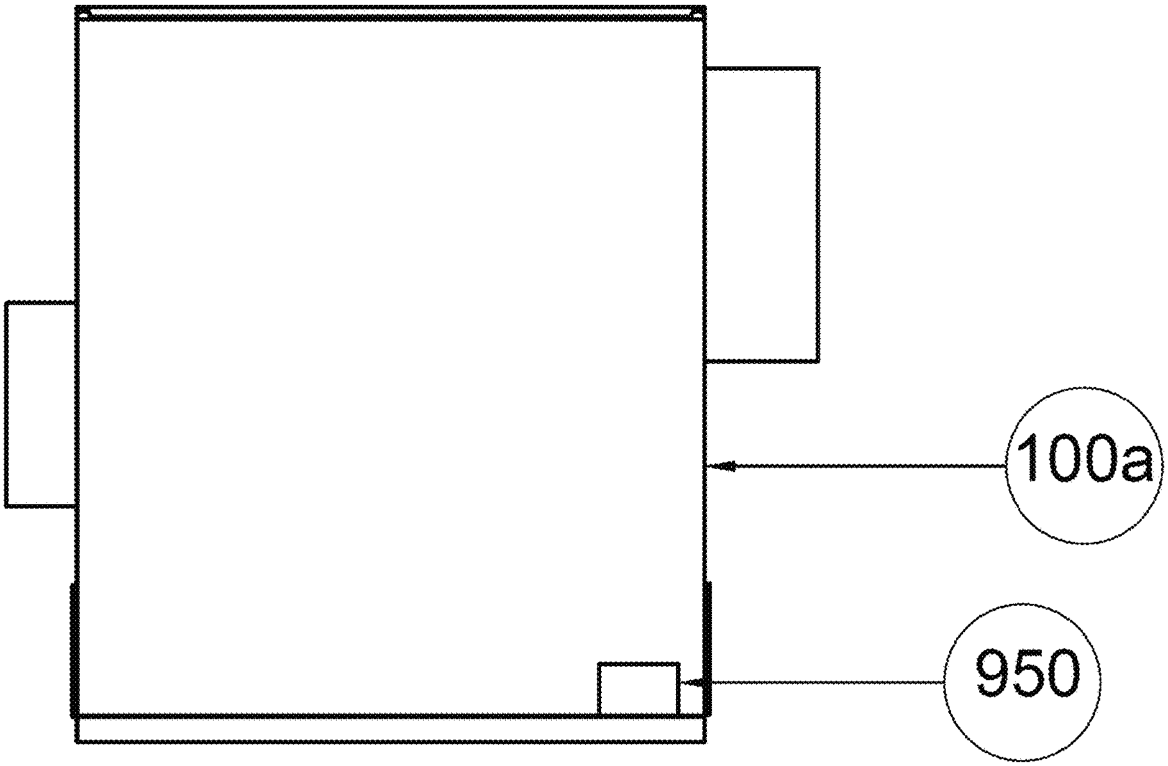
FIG. 4 is a rear view of the system, in accordance with embodiments of the present disclosure.

As further illustrated in FIGS. 2 and 3, a camera 200 and a microphone 205 are integrated into the housing to support telehealth functionalities. These components enable live audio and video communication with healthcare providers. In some embodiments, the camera 200 may also facilitate facial recognition or additional biometric identification features to enhance security and personalization.

Figure 5:
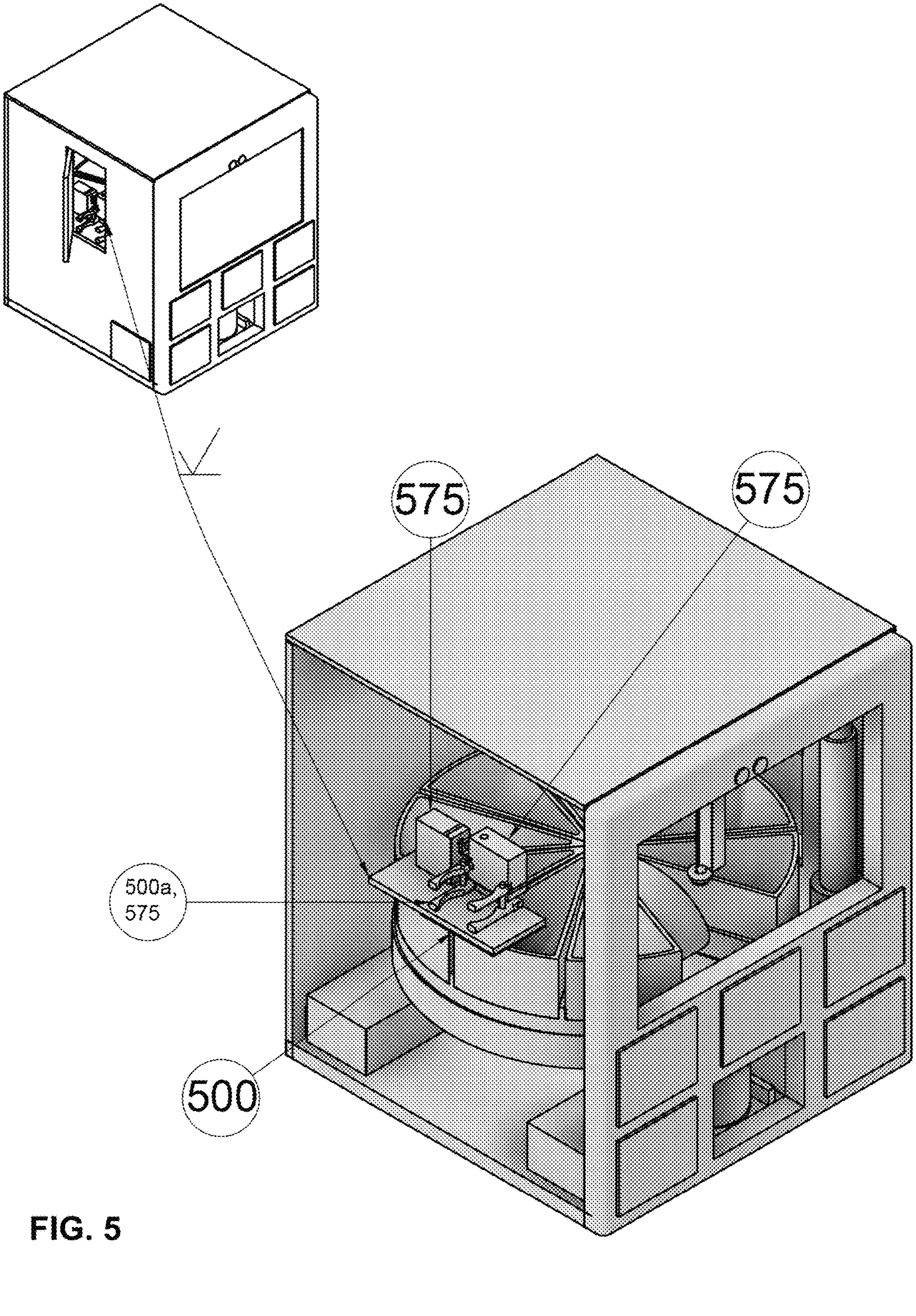
FIG. 5 is a northwest isometric perspective view of the system with the left side panel removed, in accordance with embodiments of the present disclosure.
Figure 6A:
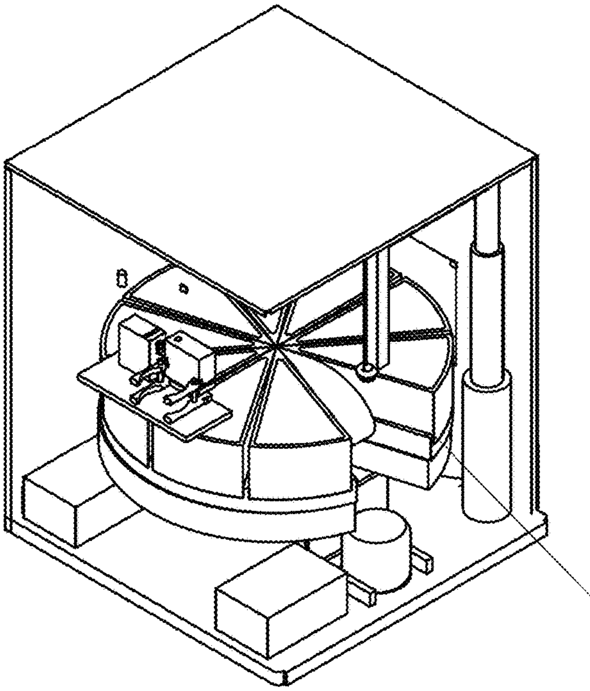
FIG. 6A is a northwest isometric perspective view of the system with the front panel removed, in accordance with embodiments of the present disclosure.

Positioned within a side intake compartment 500*a*, as seen in FIGS. 5 and 6A, is an NFC reader 500. Users place NFC-tagged medication bottles into this compartment, allowing the device to automatically read prescription data, including dosage instructions, frequency of administration, and refill information. Access to the intake compartment is provided via a magnetic door 110, which offers secure yet convenient bottle insertion. A corresponding magnetic door 110 is located on the opposite side of the device, enabling manual rapid removal of medication bottles in the event of discontinuation, malfunction, or maintenance.

Figure 6B:
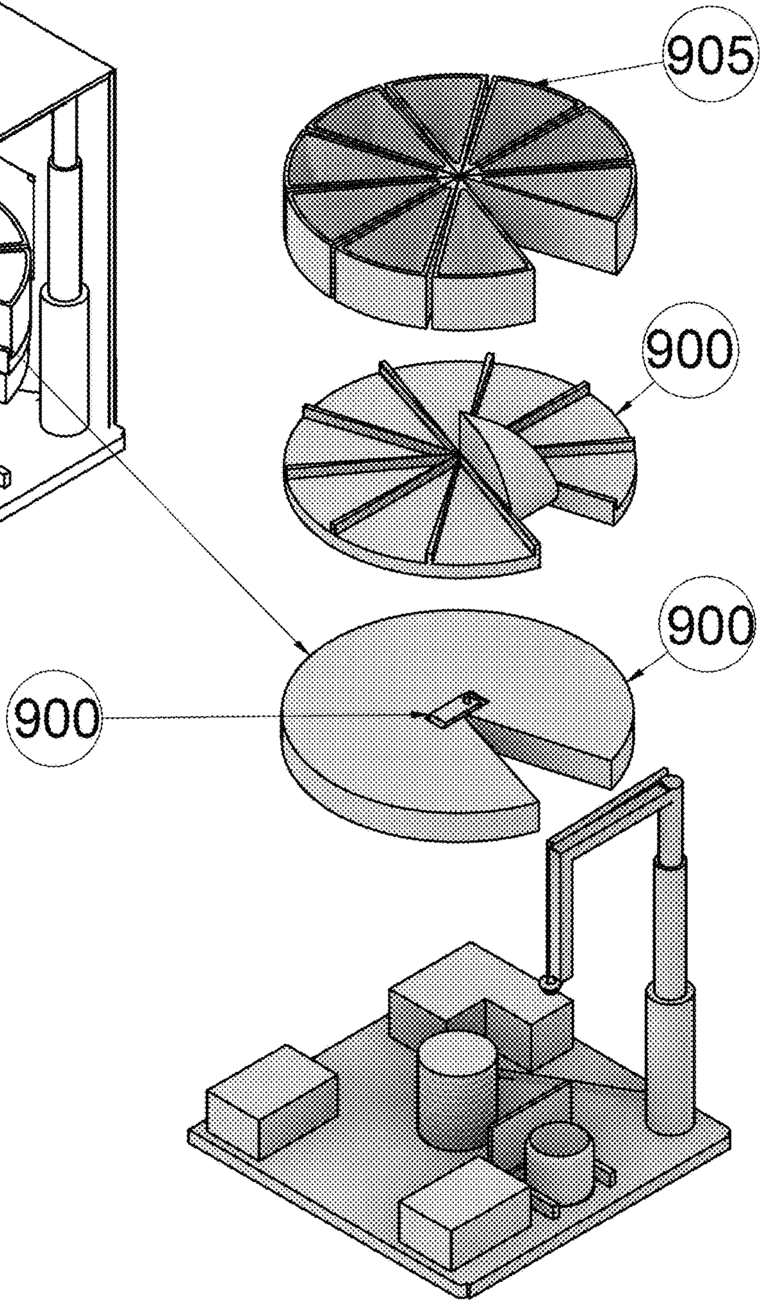
FIG. 6B is a detailed view showing internal components of the system, in accordance with embodiments of the present disclosure.
Figure 7A:
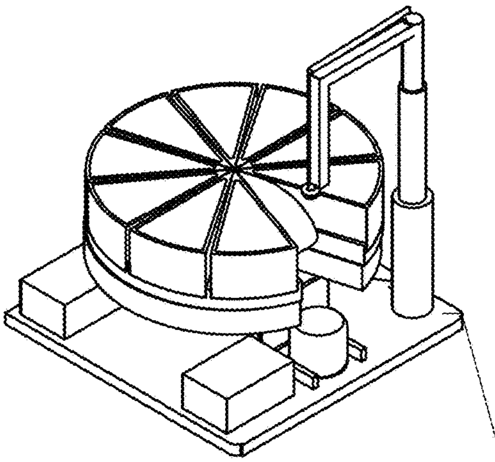
FIG. 7A is a northwest isometric perspective view of internal components of the system, in accordance with embodiments of the present disclosure.

As depicted in FIGS. 6B and 7A, a mechanical arm 575, controlled by the single-board computer 600, transfers the medication from the intake compartment to a rotational storage tray 900. The mechanical arm is equipped with feedback sensors that detect successful gripping of a bottle and can estimate bottle size. If the arm fails to grip a bottle or senses an unexpected dimension, the single-board computer 600 coordinates a prompt on the touchscreen panel to initiate additional gripping attempts or alert the user.

The rotational storage tray 900, illustrated in FIGS. 6B and 7A, is divided into wedge-shaped compartments 905, each compartment designated for a particular medication type. The tray 900 rotates about a central axis to align the appropriate compartment beneath the dispensing mechanism as required for scheduled doses.

Figure 7B:
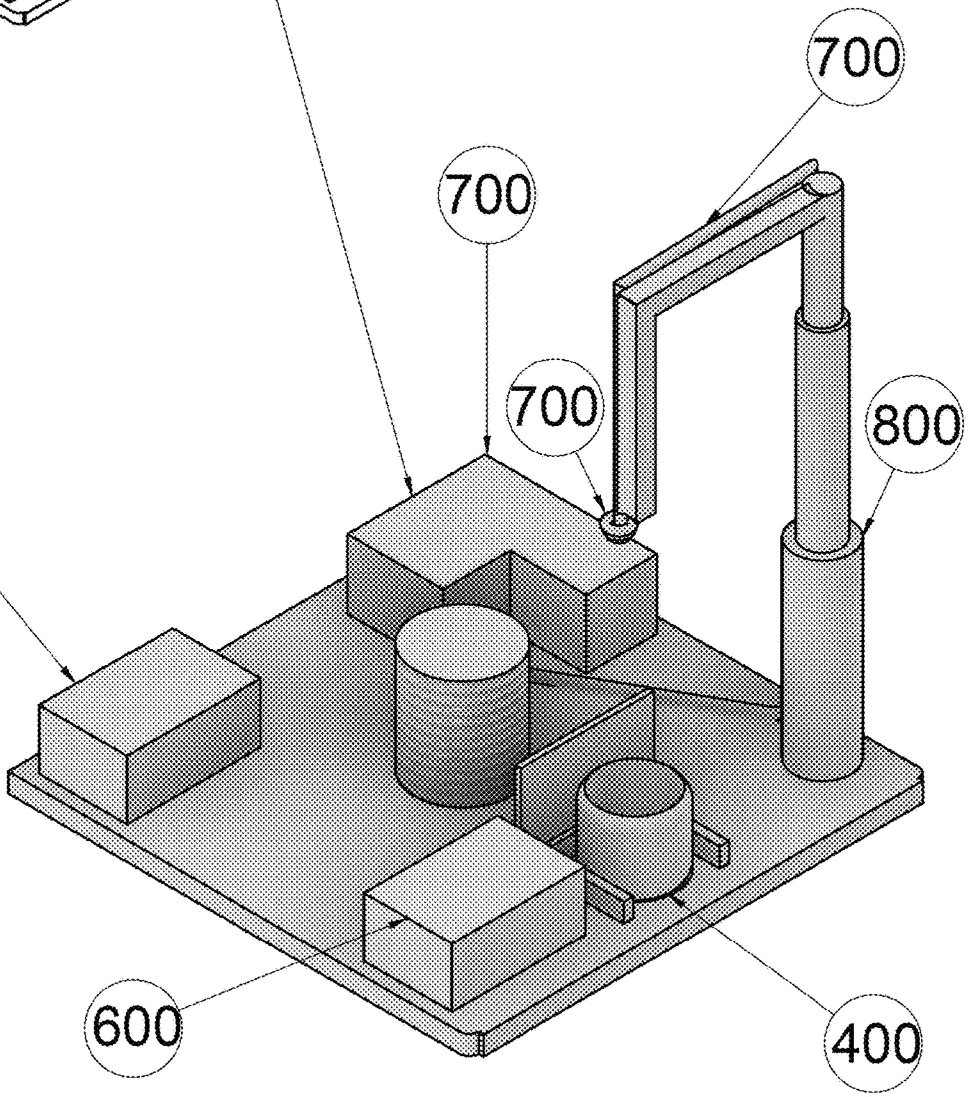
FIG. 7B is a northwest isometric perspective view of internal components with the rotational storage trays and bins removed, in accordance with embodiments of the present disclosure.
Figure 8:
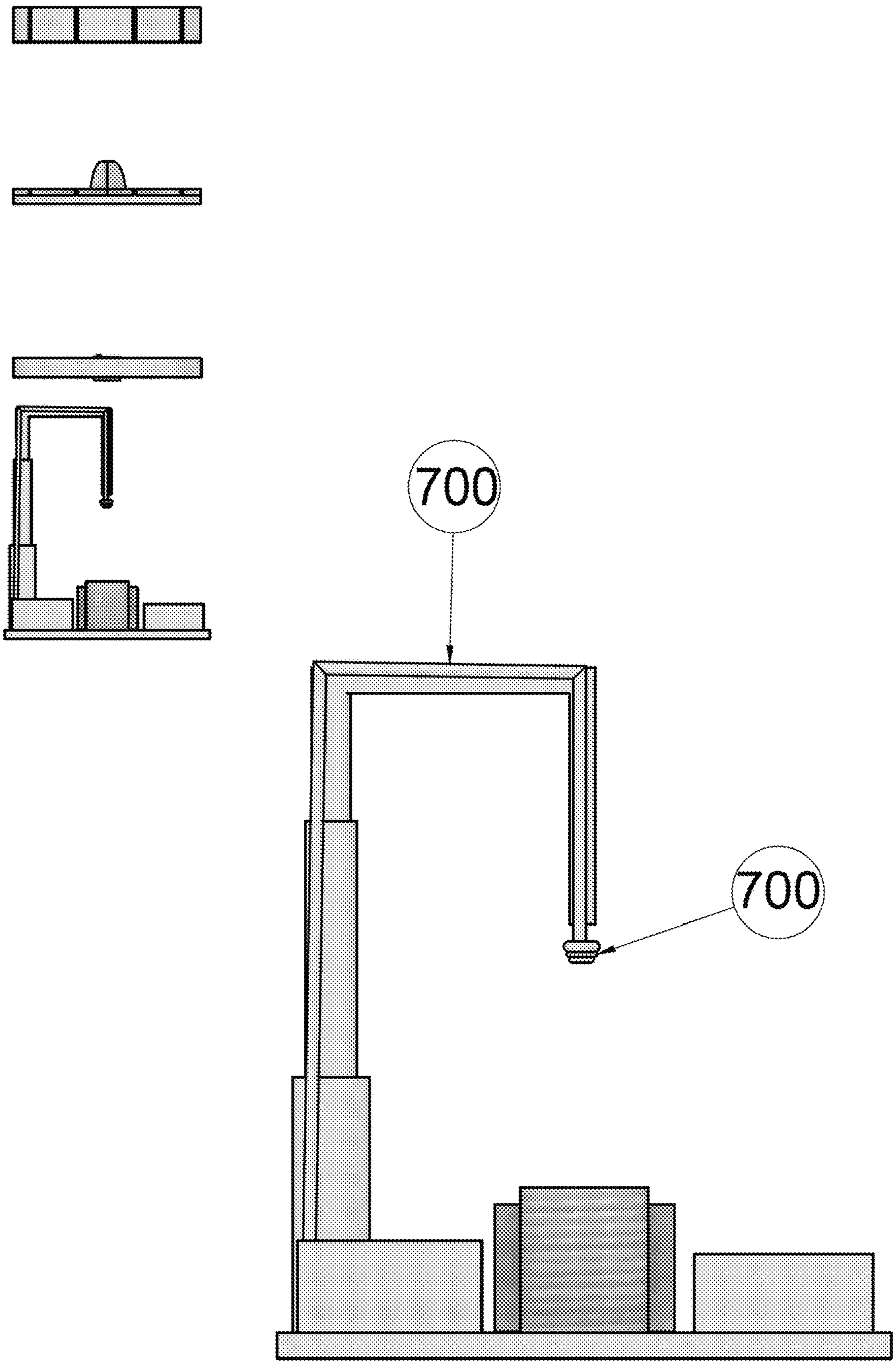
FIG. 8 is a rear isometric perspective view showing internal components of the system with external panels removed, in accordance with embodiments of the present disclosure.

A vacuum mechanism 700, detailed in FIGS. 7A and 7B, is employed to retrieve pills from the compartments of the tray 900. The vacuum's strength is dynamically managed by the single-board computer 600 to ensure consistent and reliable retrieval. If the system fails to detect successful pickup of a pill, the vacuum operation may be automatically repeated. The linear motion of the vacuum nozzle is controlled by a motor 800, enabling precise vertical movement during the dispensing process.

The system also supports an array of interchangeable vital sign monitoring modules 300, which may include modules for measuring blood pressure, heart rate, blood oxygen saturation, blood glucose levels, electrocardiogram (ECG) data, respiratory rate, fall detection, weight, and continuous insulin monitoring. Each module interfaces with the single-board computer 600, feeding real-time biometric data for display on the touchscreen panel and optional cloud-based storage and analysis.

System control is centralized within the single-board computer 600, which manages all hardware operations, software execution, data collection, user notifications, and network communications. A power distribution unit 950 supplies electrical power to critical system components including the touchscreen panel 100, motors 575 and 800, vacuum mechanism 700, and health modules 300. An integrated uninterruptible power supply (UPS) within the unit 950 ensures system functionality is maintained during power interruptions, preserving essential dispensing operations and data integrity.

In operational use, the intake and management of prescriptions begins when a user opens the magnetic door 110 and places an NFC-tagged medication bottle into the intake compartment 500*a*. The NFC reader 500 scans the bottle's prescription information, which is then stored both locally within the single-board computer 600 and optionally uploaded to a secure cloud platform.

Following prescription intake, the mechanical arm 575, guided by control logic within the single-board computer 600, grips the bottle and verifies successful engagement through feedback sensors. If a gripping failure is detected, the system may automatically initiate reattempts and issue a user notification on the touchscreen panel.

Medications are then transferred from the intake compartment to the rotational storage tray 900. Each medication is stored in a designated wedge-shaped compartment 905, and the single-board computer 600 records the associated storage location. At scheduled dosage times, the single-board computer 600 rotates the tray 900 to position the appropriate compartment beneath the vacuum retrieval mechanism 700. The vacuum system extracts the required medication and deposits it into a dispensing cup accessible to the user. If the user fails to retrieve the medication, or if the system cannot confirm successful dispensing, retry protocols and external alerts, such as text messages or app notifications, may be triggered.

At predefined intervals or user-initiated prompts, the system encourages patients to record biometric data using one or more attached health monitoring modules 300. The camera 200 and microphone 205 may also be activated to conduct remote telehealth consultations directly through the device.

All critical data events, including NFC scans, dispensing activities, and vital sign readings, are logged by the single-board computer 600 and uploaded to a secure cloud environment. Authorized caregivers and healthcare providers can access this data in real time to monitor medication adherence, assess biometric trends, and support clinical decision-making. The system may also automate prescription refill notifications and supply alerts when medication levels approach depletion, ensuring uninterrupted patient care.

In one exemplary embodiment, the automatic medication intake and dispensing system incorporates mechanical arms 575 guided by servo feedback sensors 580. The mechanical arms are configured to securely grip medication bottles, accurately detect bottle dimensions, and precisely transfer medications into assigned compartments 905 of the rotational storage tray 900. This configuration minimizes handling errors and ensures accurate medication sorting and compartmentalization, thereby improving overall dispensing reliability.

In another exemplary embodiment, the system further integrates artificial intelligence-driven adherence monitoring. The single-board computer 600 analyzes medication dispensing patterns over time. Upon detection of repeated non-adherence events or multiple missed doses, the system initiates proactive interventions, including automated telehealth interactions through the integrated high-definition camera 200 and microphone 205. Additionally, immediate notifications may be sent to caregivers or healthcare providers to enable prompt intervention and support patient adherence.

Another embodiment focuses on enhancing the reliability of medication dispensing across various pill shapes and sizes. In this embodiment, a high-powered vacuum mechanism 700 is utilized to retrieve medications from the rotational storage tray 900. The mechanical grippers are employed specifically to intake medication bottles and pour medications into the rotational compartments. To further facilitate efficient and consistent medication suction and dispensing, the system may incorporate a supplemental design comprising a specialized rubber grip coupled with the vacuum nozzle, enhancing the stability and success rate of pill retrieval operations.

In a further embodiment directed to comprehensive health monitoring, the system integrates continuous monitoring capabilities for multiple vital signs and biometric indicators. These may include modules such as a blood pressure sensor 310, heart rate sensor 315, pulse oximeter 320, temperature sensor 325, glucose sensor 330, ECG monitor 335, respiratory sensor 340, fall detection sensor 345, weight scale 350, and on-body insulin sensor 355. The single-board computer 600 monitors these parameters in real time, detects abnormal trends or critical health events, and generates immediate alerts to the user and authorized healthcare providers, enabling timely intervention and enhanced patient safety.

An additional embodiment emphasizes advanced telehealth functionality. The system incorporates a high-definition camera 200 and a high-sensitivity microphone 205 specifically designed for optimized remote patient-provider communications. This configuration ensures clear and reliable audio-visual transmission, facilitating routine patient check-ins, virtual consultations, and rapid healthcare response in both home and clinical environments.

These exemplary embodiments illustrate the diverse configurations and specialized functionalities achievable with the automatic medication intake and dispensing system. They demonstrate the adaptability of the system across a range of healthcare environments, patient needs, and medication management scenarios. Furthermore, they highlight the comprehensive integration of secure NFC-based prescription management, precise mechanical bottle intake and medication handling, reliable automated dispensing mechanisms, proactive adherence monitoring, continuous and versatile health data acquisition, and robust telehealth capabilities.

By merging secure prescription scanning through the NFC reader 500, feedback-controlled mechanical intake via the mechanical arm 575, linear vacuum-assisted dispensing utilizing the vacuum mechanism 700 and motor 800, rotational medication storage using the storage tray 900, telehealth functionality supported by the camera 200, microphone 205, and touchscreen interface 100, and interchangeable vital sign monitoring modules 300, all orchestrated by a single-board computer 600, the automatic medication intake and dispensing system provides a robust and comprehensive solution for automated medication adherence, continuous health monitoring, and remote medical engagement. The integration of these subsystems within a unified platform ensures precise medication management, timely biometric data acquisition, and seamless communication with healthcare providers, thereby enhancing patient outcomes and supporting proactive clinical interventions.

The single-board computer 600 is configured to manage, control, and coordinate operations of the automatic medication intake and dispensing system. In accordance with embodiments of the present disclosure, the single-board computer 600 may comprise at least one processor, system memory, persistent storage, and a set of input/output (I/O) interfaces. The single-board computer 600 may execute machine-readable instructions stored in memory to control mechanical operations, monitor dispensing schedules, receive and process biometric data, and manage user interactions through the touchscreen panel 100. The single-board computer 600 is operatively coupled to peripheral components including, but not limited to, the NFC reader 500, mechanical arm 575, vacuum mechanism 700, linear motion motor 800, rotational storage tray 900, vital sign monitoring modules 300, camera 200, microphone 205, and power management components 950. Communication between the single-board computer 600 and peripheral devices may be achieved through wired protocols such as serial communication (e.g., UART, SPI, or I2C), USB connections, or wireless protocols such as Wi-Fi, Bluetooth, or Zigbee.

In some embodiments, the single-board computer 600 may employ modular software architecture to facilitate separate control layers for intake management, dispensing coordination, health monitoring, telehealth communications, and system diagnostics. Additionally, the single-board computer 600 may incorporate machine learning algorithms or adaptive feedback control to optimize medication dispensing reliability and adherence interventions based on historical user behavior patterns. The single-board computer 600 may further perform real-time decision-making to adjust system parameters, such as vacuum strength or retry attempts, based on sensor feedback during mechanical operations. The single-board computer 600 may securely transmit logged events, biometric measurements, and system alerts to a remote cloud platform for external monitoring by patients, caregivers, or healthcare providers, using encrypted communication protocols to maintain data security and patient privacy. In this manner, the single-board computer 600 enables comprehensive, intelligent, and adaptive management of the system's medication adherence and health monitoring functions.

In some embodiments, the processor may be implemented as part of a single-board computer, while in other embodiments, the processor may comprise one or more discrete microcontrollers, microprocessors, or application-specific integrated circuits (ASICs) configured to perform the disclosed operations.

In accordance with embodiments of the present disclosure, and with reference to FIGS. 1-8, the automatic medication intake, dispensing, and health monitoring system, as well as its method of operation, may be further characterized as follows.

In accordance with embodiments of the present disclosure, a system for automated medication intake, dispensing, and health monitoring is provided. The system includes a housing including a touchscreen panel configured to display information and receive user inputs, an intake compartment including an NFC reader configured to scan prescription data from an NFC-tagged medication bottle, a mechanical arm operatively coupled to the intake compartment, the mechanical arm configured to transfer a medication to a rotational storage tray, the rotational storage tray including a plurality of wedge-shaped compartments configured to store different medications, a vacuum mechanism configured to retrieve medications from the rotational storage tray, a motor configured to control linear movement of the vacuum mechanism, one or more vital sign monitoring modules configured to collect biometric data from a user, and one or more processors operatively coupled to the touchscreen panel, NFC reader, mechanical arm, rotational storage tray, vacuum mechanism, motor, and vital sign monitoring modules, the one or more processors configured to manage medication intake, dispensing, health monitoring, and data communication operations.

In some embodiments, the system may further include the mechanical arm having one or more feedback sensors configured to detect successful gripping of the medication bottle. The rotational storage tray may be configured to rotate about a central axis to align a selected compartment with the vacuum mechanism for dispensing. The vacuum mechanism may include a vacuum pump and nozzle tip configured to retrieve medications from the rotational storage tray. The touchscreen panel may be further configured to prompt a user to perform vital sign measurements based on a schedule. The vital sign monitoring modules may include at least one of a blood pressure sensor, heart rate sensor, pulse oximeter, glucose sensor, ECG monitor, respiratory sensor, fall detection sensor, weight scale, or on-body insulin sensor. The system may further include a power management unit configured to provide backup power to the touchscreen panel, the one or more processors, and critical dispensing components during a power outage.

Further embodiments include a system for automated medication dispensing. The system includes an intake compartment including an NFC reader configured to receive prescription data from an NFC-tagged medication bottle, a mechanical arm including feedback sensors configured to grip a medication bottle and transfer the medication to a rotational storage tray including a plurality of wedge-shaped compartments, a vacuum mechanism including a vacuum pump and a nozzle tip, the vacuum mechanism configured to retrieve a medication from a selected compartment of the rotational storage tray, a motor configured to control linear movement of the vacuum mechanism, and one or more processors configured to control the mechanical arm, rotational storage tray, vacuum mechanism, and motor to dispense medications according to a stored schedule.

In some embodiments, the mechanical arm may be configured to initiate a retry attempt if feedback sensors detect a failed gripping event. The one or more processors may be configured to adjust a vacuum strength of the vacuum mechanism based on sensor feedback during a medication retrieval operation. The rotational storage tray may be configured to rotate about a central vertical axis to sequentially align compartments with the vacuum mechanism. The system may further include a dispensing cup positioned to receive medications retrieved by the vacuum mechanism. The intake compartment may include a magnetic door configured to secure medication bottles within the intake compartment during scanning.

Additional embodiments provide a method of operating an automated medication intake, dispensing, and health monitoring system using one or more processors. The method includes receiving prescription data from an NFC reader scanning an NFC-tagged medication bottle, storing the prescription data in a data repository, generating a medication dispensing schedule based on the prescription data, controlling a mechanical arm to transfer a medication associated with the prescription data to a rotational storage tray including a plurality of wedge-shaped compartments, rotating the rotational storage tray to align a selected compartment with a vacuum mechanism, controlling the vacuum mechanism and a motor to retrieve the medication from the selected compartment at a scheduled time, detecting a success or failure of medication retrieval, collecting biometric data from one or more vital sign monitoring modules, and uploading data related to prescription intake, dispensing events, and biometric data to a remote cloud platform via an encrypted communication link.

In some embodiments, the method may further include prompting a user via a touchscreen panel to retrieve dispensed medication. The method may further include initiating a retry protocol to reattempt medication retrieval upon detection of a retrieval failure. The method may further include adjusting a vacuum strength of the vacuum mechanism based on sensor feedback during medication retrieval. The method may further include generating a notification to a caregiver or healthcare provider upon detection of a missed dose. The method may further include performing facial recognition authentication of the user prior to dispensing the medication. The method may further include prompting the user, via the touchscreen panel, to perform a scheduled vital sign measurement.

Further embodiments provide a method of monitoring medication adherence and dispensing status in an automated system using one or more processors. The method includes receiving prescription data from an NFC reader scanning an NFC-tagged medication bottle, storing dispensing schedule data associated with the prescription data, detecting an occurrence of a scheduled dispensing event, determining, based on sensor feedback, whether a medication retrieval associated with the dispensing event has occurred, initiating a retry protocol if the medication retrieval is not detected, generating an adherence record based on retrieval success or failure, and uploading adherence records to a remote server.

In some embodiments, the method may further include generating a user alert on a touchscreen panel when a medication retrieval failure is detected. The method may further include automatically adjusting retry parameters based on historical retrieval failure patterns. The method may further include compiling adherence data into a longitudinal patient adherence profile stored in the remote server. The method may further include encrypting the adherence records prior to uploading to the remote server.

Further embodiments provide a system for performing the method of monitoring medication adherence and dispensing status as described above. The system includes an NFC reader configured to scan prescription data from an NFC-tagged medication bottle, a mechanical arm configured to transfer a medication to a rotational storage tray including a plurality of wedge-shaped compartments, a vacuum mechanism configured to retrieve a medication from a selected compartment of the rotational storage tray, a motor configured to control linear movement of the vacuum mechanism, and one or more processors operatively coupled to the NFC reader, mechanical arm, rotational storage tray, vacuum mechanism, and motor, the one or more processors configured to store dispensing schedule data associated with the prescription data, detect an occurrence of a scheduled dispensing event, determine, based on sensor feedback, whether a medication retrieval associated with the dispensing event has occurred, initiate a retry protocol if the medication retrieval is not detected, generate an adherence record based on retrieval success or failure, and upload the adherence record to a remote server.

In some embodiments, the system may further include the one or more processors being configured to generate a user alert on a touchscreen panel when a medication retrieval failure is detected. The one or more processors may further be configured to automatically adjust retry parameters based on historical retrieval failure patterns. The one or more processors may further be configured to compile adherence data into a longitudinal patient adherence profile stored in the remote server. The one or more processors may further be configured to encrypt the adherence records prior to uploading to the remote server.

Figure 9:
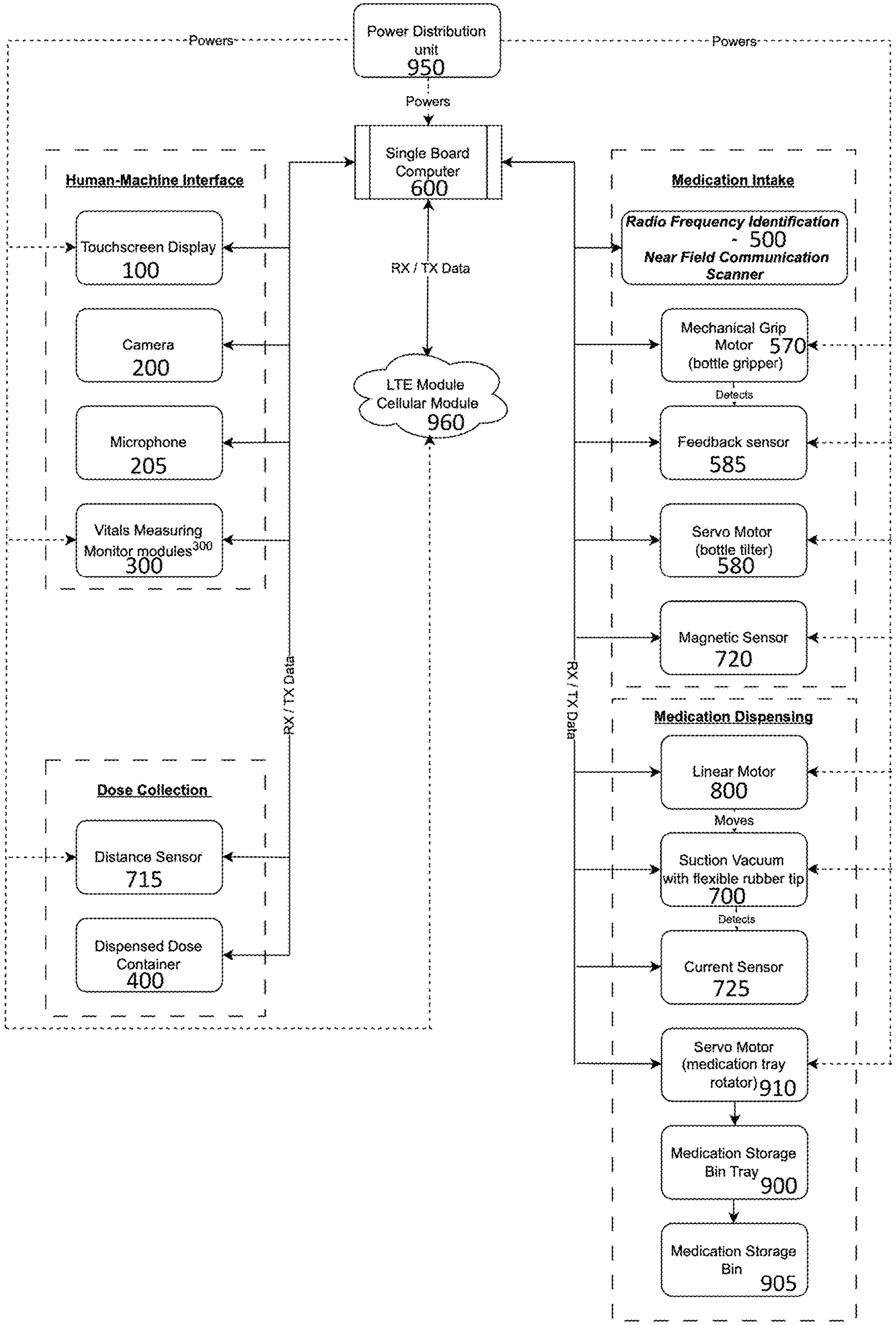
FIG. 9 is a system-level hardware diagram illustrating components of the automated medication intake and dispensing system in accordance with embodiments of the present disclosure.

Referring now to FIG. 9, the system includes multiple hardware components configured to enable automated medication intake, dispensing, and health monitoring in accordance with embodiments of the present disclosure. A single-board computer 600 serves as the central control unit and is operatively coupled to all major subsystems. The single-board computer 600 is responsible for coordinating prescription intake, mechanical actuation, feedback response, vital sign monitoring, data storage, and communication operations.

The system includes a near-field communication (NFC) scanner 500, positioned within the intake compartment 500*a*, configured to scan NFC tags on medication bottles to extract prescription data such as dosage, timing, and identification parameters. Mechanical intake operations are performed using a mechanical gripping motor 570, which actuates a bottle gripper 575 to grasp the medication bottle. A servo motor 580 is used to tilt the bottle as needed, for example, during a pouring operation. A feedback sensor 585 provides real-time data regarding bottle position, tilt angle, and grip status to the single-board computer 600.

A linear motor 800 controls the vertical movement of a vacuum-based medication retrieval mechanism 700. The vacuum mechanism includes a flexible rubber suction tip configured to extract individual medication doses from designated compartments in a rotational medication storage tray 900. The storage tray 900 is rotated using a servo motor 910, which aligns the selected compartment 905 under the vacuum mechanism 700 for dispensing. The retrieved medication is delivered into a dispensed dose container 400.

A distance sensor 715 and magnetic sensor 720 are included to monitor proximity and alignment of moving parts, such as confirming when the tray 900 is in position or when the suction tip is properly engaged. A current sensor 725 monitors power draw from various motors and actuators to detect anomalies such as motor stalls or failed grip attempts.

The system is further configured to collect biometric data from the user via one or more interchangeable vital sign monitoring modules 300. These modules may include, for example, a blood pressure sensor, heart rate sensor, pulse oximeter, or other physiological measurement devices. The touchscreen display 100 provides a graphical interface through which the user may receive prompts, alerts, or review medication schedules and health metrics. A camera 200 and microphone 205 are integrated to support telehealth functionality, including real-time video consultations and audio feedback.

Communication with external systems such as cloud-based databases or caregiver dashboards may be established through an LTE module 960 or alternative cellular or wireless data interface. The system includes a power distribution unit 950 that supplies regulated power to all components, and may optionally include a backup power source to ensure continued operation during outages.

FIG. 9 also illustrates logical groupings such as the medication intake region, medication dispensing components, and the human-machine interface, along with interconnections for data (e.g., RX/TX), power delivery, and feedback signaling between modules.

In combination, the hardware components shown in FIG. 9 enable the system to receive and authenticate prescription inputs, mechanically manipulate medication containers, accurately dispense scheduled doses, monitor vital signs, engage in telehealth sessions, and upload critical data to secure storage platforms for caregiver access.

Figure 10:
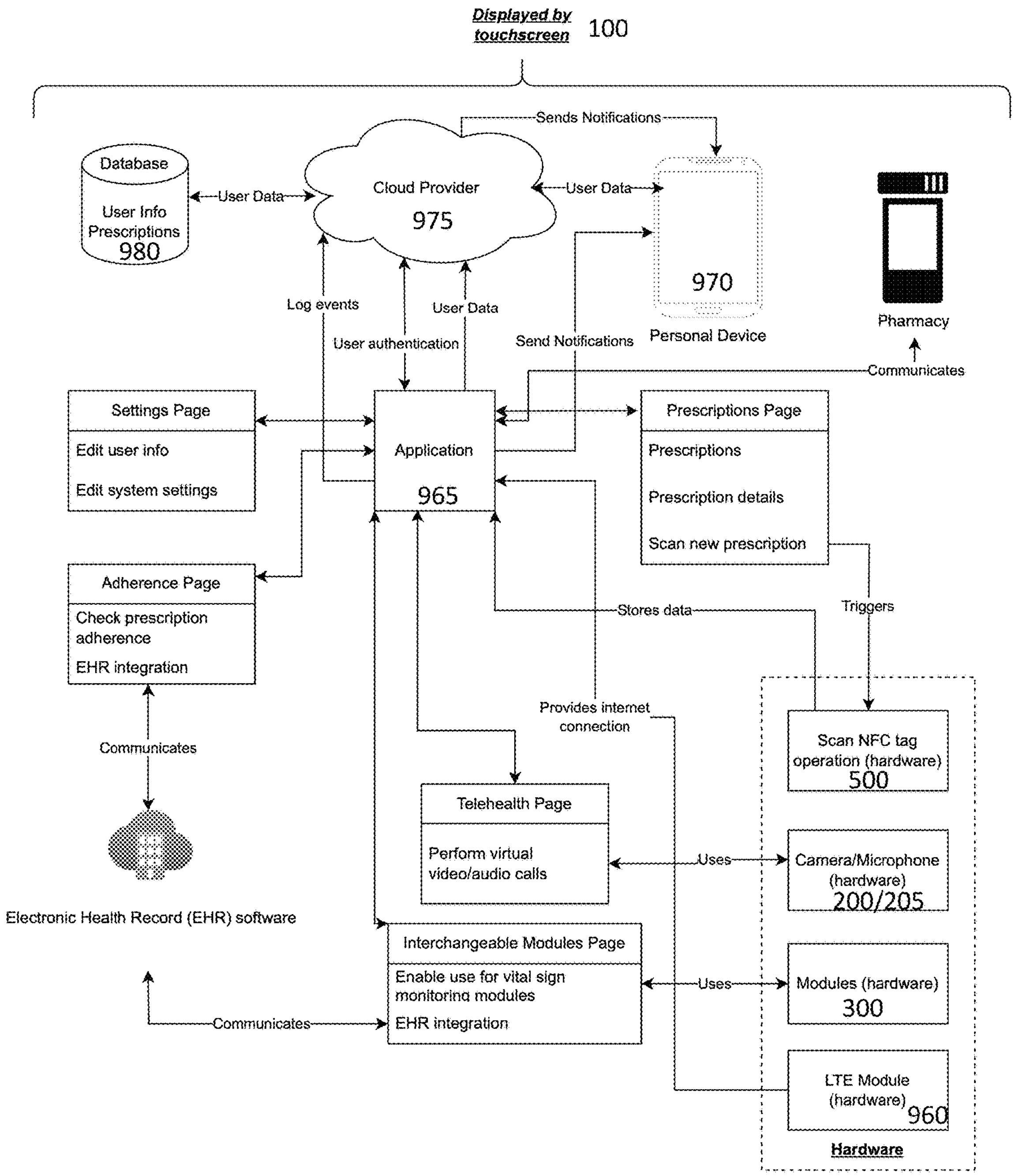
FIG. 10 is a software architecture and data flow diagram illustrating logical interactions among various software modules, hardware interfaces, user inputs, and external systems in accordance with embodiments of the present disclosure.

Referring now to FIG. 10, the software architecture of the automated medication intake, dispensing, and health monitoring system is illustrated in accordance with embodiments of the present disclosure. This architecture is executed by one or more processors 600 and coordinates data flow, hardware control, user interaction, cloud communication, and adherence tracking.

The user interacts with the system primarily through the touchscreen panel 100, which provides access to multiple application-layer modules. These modules include prescription scanning, medication adherence tracking, system settings management, telehealth integration, and biometric data collection. These modules are executed under processor control and are displayed through a graphical interface presented to the user.

Prescription data is captured via the NFC reader 500 located within intake compartment 500*a*. When an NFC-tagged medication bottle is placed in the compartment, the reader scans the encoded data, which includes dosage, frequency, and other identifiers. This data is stored by the processor 600 and used to generate a medication dispensing schedule. At scheduled intervals, the processor controls the mechanical arm 575, linear motor 800, and vacuum mechanism 700 to retrieve medication from the appropriate compartment within the rotational storage tray 900.

Sensor feedback is used to detect whether a medication retrieval event has succeeded or failed. This may include input from grip feedback sensors 585, distance sensors 715, magnetic sensors 720, or current sensors 725. If a failure is detected, the processor may trigger a retry protocol, generate an alert, and log the event for compliance monitoring. All retrieval and retry events may be stored in a secure event log and analyzed for adherence behavior.

The software system also includes a biometric monitoring interface. Users may be prompted via the touchscreen 100 to initiate a measurement using one or more health modules 300, such as blood pressure, heart rate, or blood oxygen sensors. The measured data is processed by the processor 600 and may be displayed locally or transmitted securely to a remote cloud platform via the LTE module 960 for review by caregivers or healthcare providers.

Telehealth functionality is optionally available through an integrated video and audio communication interface. The camera 200 and microphone 205 enable real-time consultations, video-based dose confirmations, or patient check-ins. The LTE module provides encrypted internet connectivity to support secure remote sessions and integration with external healthcare infrastructure.

The system further allows users or administrators to manage user profiles and system configuration settings. These may include notification preferences, schedule adjustments, authentication options, and accessibility features. Authentication may optionally be performed via facial recognition using the onboard camera 200 or manual input through the touchscreen.

All software-controlled operations-prescription intake, medication dispensing, retry handling, biometric data collection, and adherence logging are managed by the processor 600 and executed in accordance with one or more methods of the present disclosure. These methods enable comprehensive system behavior that ensures accurate dispensing, active monitoring of user compliance, and seamless communication with cloud-based healthcare systems. FIG. 10 illustrates the flow of information and control between user interfaces, physical hardware, sensor feedback, and external systems, providing a logical foundation for intelligent and reliable medication management.

As further shown in FIG. 10, the system communicates with a set of external computing and storage resources that support remote monitoring, data synchronization, and user interaction beyond the local device. A personal device 970, such as a smartphone, tablet, or caregiver terminal, may be used to access system status, receive alerts, or interact with the system through a secure application interface. The system is connected to a cloud platform 975, which serves as a remote infrastructure layer for data management, software updates, and cross-device coordination. A cloud-hosted database 980 stores records related to prescription intake, medication dispensing history, adherence events, biometric measurements, and telehealth interactions. Data is transmitted between the system and the cloud provider 975 via the LTE module 960, using encrypted protocols to ensure data privacy and regulatory compliance. These external elements enable continuous oversight, real-time intervention by caregivers, and long-term storage of user-specific health and medication records in accordance with embodiments of the present disclosure.

An application module 965, as shown in FIG. 10, is executed by the processor 600 and serves as the primary software control layer for the system. The application 965 manages user interface logic, scheduling routines, sensor feedback processing, retry protocols, biometric data collection, and secure communication with external platforms. It coordinates interactions between the touchscreen panel 100, NFC reader 500, motors, sensors, and connected components such as the camera 200, microphone 205, and vital sign monitoring modules 300. The application 965 also serves as the integration point for cloud synchronization via the LTE module 960 and enables user and caregiver interaction through personal device 970 and cloud platform 975. In accordance with embodiments of the present disclosure, the application 965 governs execution of automated methods related to prescription intake, adherence detection, health monitoring, and remote reporting.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

The foregoing detailed description is merely exemplary in nature and is not intended to limit the invention or application and uses of the invention. Furthermore, there is no intention to be bound by any expressed or implied theory presented in the preceding technical field, background, brief summary, or the following detailed description.

The invention claimed is:

1. A method of operating an automated medication intake, dispensing, and health monitoring system using one or more processors, the method comprising:

receiving prescription data from an NFC reader scanning an NFC-tagged medication bottle;

storing the prescription data in a data repository;

generating a medication dispensing schedule based on the prescription data;

controlling a mechanical arm to transfer a medication associated with the prescription data to a rotational storage tray comprising a plurality of wedge-shaped compartments;

rotating the rotational storage tray to align a selected compartment with a vacuum mechanism;

controlling the vacuum mechanism and a motor to retrieve the medication from the selected compartment at a scheduled time;

detecting a success or failure of medication retrieval;

collecting biometric data from one or more vital sign monitoring modules; and uploading data related to prescription intake, dispensing events, and biometric data to a remote cloud platform via an encrypted communication link.

2. The method of claim 1, further comprising prompting a user via a touchscreen panel to retrieve dispensed medication.

3. The method of claim 1, further comprising initiating a retry protocol to reattempt medication retrieval upon detection of a retrieval failure.

4. The method of claim 1, further comprising adjusting a vacuum strength of the vacuum mechanism based on sensor feedback during medication retrieval.

5. The method of claim 1, further comprising generating a notification to a caregiver or healthcare provider upon detection of a missed dose.

6. The method of claim 1, further comprising performing facial recognition authentication of the user prior to dispensing the medication.

7. The method of claim 1, further comprising prompting the user, via the touchscreen panel, to perform a scheduled vital sign measurement.

8. A system for operating an automated medication intake, dispensing, and health monitoring process, comprising:
- an NFC reader configured to scan prescription data from an NFC-tagged medication bottle;
- a mechanical arm configured to transfer a medication associated with the prescription data to a rotational storage tray comprising a plurality of wedge-shaped compartments;
- a vacuum mechanism configured to retrieve the medication from a selected compartment of the rotational storage tray;
- a motor configured to control linear movement of the vacuum mechanism;
- one or more vital sign monitoring modules configured to collect biometric data from a user;
- a touchscreen panel configured to display information and receive user inputs; and
- one or more processors operatively coupled to the NFC reader, mechanical arm, rotational storage tray, vacuum mechanism, motor, vital sign monitoring modules, and touchscreen panel, the one or more processors configured to:
  - store the prescription data;
  - generate a medication dispensing schedule based on the prescription data;
  - control the mechanical arm, rotational storage tray, vacuum mechanism, and motor to dispense medication at scheduled times;
  - detect a success or failure of medication retrieval;
  - collect biometric data from the one or more vital sign monitoring modules; and
  - upload data related to prescription intake, dispensing events, and biometric data to a remote cloud platform via an encrypted communication link.

9. The system of claim 8, wherein the touchscreen panel is further configured to prompt the user to retrieve dispensed medication.

10. The system of claim 8, wherein the one or more processors are configured to initiate a retry protocol upon detection of a medication retrieval failure.

11. The system of claim 8, wherein the one or more processors are configured to adjust a vacuum strength of the vacuum mechanism based on sensor feedback during medication retrieval.

12. The system of claim 8, wherein the one or more processors are configured to generate a notification to a caregiver or healthcare provider upon detection of a missed dose.

13. The system of claim 8, wherein the one or more processors are configured to perform facial recognition authentication of a user prior to dispensing the medication.

14. The system of claim 8, wherein the one or more processors are configured to prompt the user to perform scheduled vital sign measurements via the touchscreen panel.

* * * * *